United States Patent [19]

Trepka et al.

[11] Patent Number: 5,422,389
[45] Date of Patent: Jun. 6, 1995

[54] METHOD FOR STABILIZING MONOVINYLARENE/CONJUGATED DIENE COPOLYMERS AND A METHOD FOR PREPARING A STABILIZING MIXTURE

[75] Inventors: William J. Trepka; Larry L. Nash, both of Bartlesville; John R. Bohannan, Dewey; Nathan E. Stacy, Bartlesville; George A. Moczygemba, Bartlesville; Craig D. DePorter, Bartlesville, all of Okla.; Luis E. Reyes, La Porte, Tex.; Tad L. Olson, New Orleans, La.

[73] Assignee: Phillips Petroleum Company, Bartlesville, Okla.

[21] Appl. No.: 192,000

[22] Filed: Feb. 4, 1994

[51] Int. Cl.⁶ .................................... C08K 5/52
[52] U.S. Cl. ........................... 524/128; 524/575
[58] Field of Search ..................... 524/575, 128

[56] References Cited

U.S. PATENT DOCUMENTS

| | | | |
|---|---|---|---|
| 3,629,372 | 12/1971 | Drake | 260/880 |
| 3,922,249 | 11/1975 | Mills | 260/25.8 R |
| 4,584,346 | 4/1986 | Kitchen | 525/98 |
| 4,956,408 | 9/1990 | Mathis et al. | 524/147 |

FOREIGN PATENT DOCUMENTS 63-27551  2/1988  Japan .

*Primary Examiner*—Ana L. Carrillo
*Attorney, Agent, or Firm*—Marianne H. Michel

[57] ABSTRACT

A process for stabilizing polymers is provided comprising:

(1) contacting at least one hindered phenolic compound and an organic phosphite to form a stabilizing mixture,
wherein said contacting is at a temperature sufficient to at least partially dissolve said hindered phenolic compound,
wherein said stabilizing mixture is essentially free of organic solvent; and
(2) contacting said stabilizing mixture and a polymeric composition comprising a monovinylarene/-conjugated diene copolymer;
wherein said organic phosphite and said at least one hindered phenolic compound are present in step (2) in an effective amount sufficient to stabilize said polymeric composition. In accordance with another aspect of this invention a method for preparing a stabilizing mixture essentially free of organic solvent is provided.

34 Claims, No Drawings

METHOD FOR STABILIZING MONOVINYLARENE/CONJUGATED DIENE COPOLYMERS AND A METHOD FOR PREPARING A STABILIZING MIXTURE

This invention relates to a method for the stabilization of monovinylarene/conjugated diene copolymers and a method for preparing a stabilizing mixture.

BACKGROUND

Monovinylarene polymers and monovinylarene/conjugated diene copolymers are known and useful for a variety of purposes, It is also known to add various stabilizers to the polymers to prevent deterioration from prolonged use or processing at high temperatures, Previously stabilizers were dissolved in an organic solvent and added to the reaction solution prior to recovery of the polymer. A problem is encountered when employing certain stabilizers because of their low solubility in various typical organic solvents, Dissolving such stabilizers in solvent requires large amounts of organic solvent and high temperatures and pressures. Addition of such stabilizers is impractical in commercial processes and would require pressurized equipment. Employing solvents at elevated temperatures requires special considerations and handling techniques which contribute to the complexity and expense of commercial processes. Another disadvantage of employing such stabilizer solvent solutions, is that the stabilizers can precipitate from solution causing plugging of transfer lines and equipment.

It would therefore be desirable to develop a simple, inexpensive, and safe process for stabilizing polymers such as monovinylarene/conjugated diene copolymers.

SUMMARY OF THE INVENTION

It is an object of this invention to provide a commercially feasible method for stabilizing polymers such as monovinylarene/conjugated diene copolymers.

It is another object of this invention to provide a method for preparing a stabilizing mixture which does not form precipitate at ambient temperature and is easy to transfer.

In accordance with this invention a process for stabilizing polymers is provided comprising:

(1) contacting at least one hindered phenolic compound and an organic phosphite to form a stabilizing mixture,
    wherein said contacting is at a temperature sufficient to at least partially dissolve said hindered phenolic compound,
    wherein said stabilizing mixture is essentially free of organic solvent; and (2) contacting said stabilizing mixture and a polymeric composition comprising a monovinylarene/conjugated diene copolymer;
    wherein said organic phosphite and said at least one hindered phenolic compound are present in step (2) in an effective amount sufficient to stabilize said polymeric composition.

In accordance with another aspect of this invention a method for preparing a stabilizing mixture essentially free of organic solvent is provided.

DETAILED DESCRIPTION OF THE INVENTION

The organic phosphites useful in this invention are those of the formula $(RO)_3P$, wherein each R is individually selected and is an alkyl, aryl, cycloalkyl, arylalkyl, or alkylaryl radical containing 1 to 20 carbon atoms, preferably 1 to 15 carbon atoms. Preferably at least one R radical contains an aryl group. Suitable examples of such organic phosphites include tris(nonylphenyl) phosphite, diphenyl decyl phosphite, didecyl phenyl phosphite, phenyl di(2-ethylhexyl) phosphite, diisooctyl phenyl phosphite, methyl diphenyl phosphite, triphenyl phosphite, tris(2,4-dimethylphenyl) phosphite, phenyl dicyclohexyl phosphite, diisopropyl phenyl phosphite, diethyl phenyl phosphite, 2-phenylnonyl amyl dodecyl phosphite, di(2-ethylchclohexyl) n-butyl phosphite, 3-cyclopentylpropyl dihexyl phosphite, and the like or mixtures thereof. The preferred organic phosphite is tris(nonylphenyl) phosphite.

The hindered phenolic compounds useful in this invention are such as those which have in the past been employed to enhance stability in synthetic resins. Although the present invention is suitable for adding any stabilizer which is soluble in the organic phosphite, it is especially effective for adding hindered phenolic compounds which demonstrate reduced solubility in organic solvents and are therefore difficult to combine in a solution process prior to recovery of the polymer. For example, it is particularly advantageous to employ the invention with hindered phenolic compounds which exhibit a solubility of less than about 50 weight percent in cyclohexane at 50° C.

Suitable examples of hindered phenolic compounds include 2,6- di-t-butyl- 4-methylphenol, n-octadecyl 3-(3,5-di-t-butyl-4-hydroxyphenyl)propionate, tetrakis [3-(3,5-di-t-butyl-4-hydroxyphenyl)propionyloxymethyl]methane, 1,3,5-trimethyl-2,4,5-tris (3,5-di-t-butyl-4-hydroxybenzyl)benzene, thiodiethylene bis (3,5-di-t-butyl-4-hydroxy)hydrocinnamate, N'N'-bis[3'5 'di-t-butyl-4-hydroxyphenyl)propanyl-hydrazine, tris(3,5-di-t-butyl-4-hydroxybenzyl)isocyanurate, tris(2-methyl-4-hydroxy-5-t-butylphenyl)butane, tris(3-hydroxy-4-t-butyl-2,6-dimethylbenzyl)cyanurate, and mixtures thereof. The preferred hindered phenolic compound for use in this invention is tetrakis [3-(3,5-di-t-butyl-4-hydroxyphenyl)propionyloxymethyl]methane.

It is also within the scope of the invention to employ acrylate hindered phenolic compounds, either alone or in combination with the above cited hindered phenolic compounds. The acrylate hindered phenolic compounds are represented by the formula

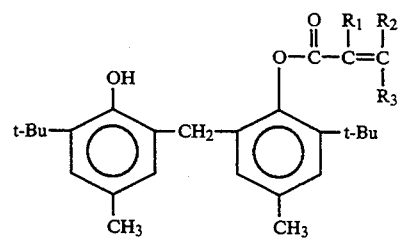

wherein t-Bu is a t-butyl group, and wherein each R is individually selected and is the same or different and is selected from the group consisting of hydrogen, alkyl, aryl, cycloalkyl, and alkyl substituted aryl radicals having from 1 to 16 carbon atoms, preferably 1 to 12 carbon atoms. Examples of suitable acrylate hindered phenolic compounds include 2-(2-hydroxy-3-t-butyl-5-methylbenzy 1)-4-methyl-6butylphenyl acrylate, 2-(2-hydroxy-3-t-butyl-5-methylbenzyl) -4-methyl-6-t-butylphenyl methacrylate, 2-(3,5-di-t-butyl-4-hydroxybenzyl)-4-methylphenyl methacrylate, 2-(3,5-di-t-butyl-4-hydroxybenzyl)-4- methylphenyl acrylate, 4-(3,5-di-t-butyl-4-hydroxybenzyl)phenyl acrylate, 2-(3,5-di-t-butyl-4-hydroxybenzyl)phenyl methacrylate, 2,6-bis(2-hydroxy-3-t-butyl-5-methylbenzyl)-4-methylphenyl methacrylate, and mixtures thereof. The preferred acrylate hindered phenolic compound is 2-(2-hydroxy-3-t-butyl-5-methylbenzyl)-4-methyl-6-t-butylphenyl acrylate.

The weight ratio of hindered phenolic compound to the organic phosphite can vary broadly depending on the solubility of the particular phenolic compound and the desired amount in the final polymer. Generally the weight ratio of hindered phenolic compound to the organic phosphite will be in the range of about 0.01:1 to about 1:1, preferably about 0.05:1 to about 0.8:1, and more preferably 0.1:1 to 0.7:1.

The hindered phenolic compound and the organic phosphite are contacted under conditions sufficient to at least partially dissolve the hindered phenolic compound in the organic phosphite. The temperature and pressure at which the hindered phenolic compound is dissolved in the organic phosphite will vary broadly depending on the solubility of the particular hindered phenolic compound.

Generally the compounds will be contacted at a temperature in the range between the temperature at which the hindered phenolic compound dissolves in the organic phosphite and up to about 50° C. above such temperature, preferably between the temperature at which the hindered phenolic compound dissolves in the organic phosphite and up to about 40° C. above such temperature, more preferably between the temperature at which the hindered phenolic compound dissolves in the organic phosphite and up to 30° C. above such temperature.

For example, when dissolving n-octadecyl 3-(3,5-di-t-butyl-4-hydroxyphenyl)propionate in tris(nonylphenyl) phosphite, suitable temperatures are in the range of about 50° C. to about 100° C., preferably from about 50° C. to about 90° C., more preferably from about 50° C. to about 80° C. When dissolving tetrakis [3-(3,5-di-t-butyl-4-hydroxyphenyl)propionyloxymethyl]methane or 2-(2-hydroxy-3-t-butyl-5-methylbenzyl)-4-methyl-6-t-butylphenyl acrylate in tris(nonylphenyl) phosphite, suitable temperatures are in the range of about 90° C. to about 140° C., preferably from about 90° C. to about 130° C., more preferably from about 90° C. to about 120° C.

The pressure employed in contacting the hindered phenolic compound and the organic phosphite can vary broadly and will depend on the temperature and particular hindered phenolic compound employed, as well as the equipment available. An advantage of the present process is that the hindered phenolic compound can be dissolved in the organic phosphite at relatively low pressures.

The stabilizing mixture of the present invention is prepared in a system essentially free of organic solvent. The term "organic solvent", as used herein, includes solvents having relatively low boiling points and high vapor pressures, i.e. boiling points below about 100° C.

Examples of such solvents include hexane, cyclohexane, heptane, acetone, and tetrahydrofuran.

After the stabilizing mixture is formed, it can be cooled and stored at ambient temperatures or transferred directly to a polymeric composition such as a monovinylarene/conjugated diene copolymer. Preferably the stabilizing mixture is transferred at a temperature sufficiently high to reduce the viscosity for ease of handling. The thus prepared stabilizing mixture does not form a precipitate, unlike stabilizing systems containing organic solvent.

For example, when the stabilizing mixture includes tetrakis [3-(3,5-di-t-butyl-4-hydroxyphenyl)propionyloxymethyl]methane and tris(nonylphenyl) phosphite, the preferred transfer temperature will be in the range of about 50° C. to about 60° C.

Monovinylarene/conjugated diene copolymers generally useful in this invention are comprised of monovinylarene/conjugated diene copolymers produced by a solution process involving sequential polymerization of a monovinylarene and a conjugated diene. Optionally, a monovinylarene monomer/conjugated diene monomer mixture can be polymerized to form a monovinylarene/conjugated diene block. In some circumstances the polymer chains can be coupled to form multimodal block copolymer having a broad molecular weight distribution.

The basic preparation of the above mentioned copolymers is disclosed in U.S. Pat. Nos. 4,584,346, 4,091,053, 4,704,434 and 4,704,435, the disclosures of which are hereby incorporated by reference.

In a preparation method typical of these publications, conjugated diene monomer and monovinylarene monomer are copolymerized sequentially in the presence of an organolithium compound and a hydrocarbon solvent at temperatures up to about 150° C.

Suitable monovinylarene monomers which can be used in the copolymers include those having 8 to 18 carbon atoms per molecule, preferably 8 to 12 carbon atoms. Examples of such suitable compounds include styrene, 3-methylstyrene, 4-n-propylstyrene, 4-cyclohexylstyrene, 4-decylstyrene, 2-ethyl-4-benzylstyrene, 4-(p-tolyl)styrene, 4-(4-phenyl-n-butyl)styrene, 1-vinylnaphthalene, 2-vinylnaphthalene, and mixtures thereof. Styrene is the preferred monovinylarene.

Suitable conjugated dienes or mixtures thereof which can be used in this invention include those having 4 to 12 carbon atoms per molecule, with those having 4 to 8 carbon atoms preferred. Examples of such suitable compounds include 1,3-butadiene, isoprene, 2,3-dimethyl-1,3-butadiene, piperylene, 3-butyl-1,3-octadiene, and the like. The preferred dienes are 1,3-butadiene and isoprene, most preferably 1,3-butadiene.

The copolymer can be resinous, i.e. containing an amount of monovinylarene greater than about 50 weight percent, or rubbery, containing an amount of conjugated diene greater than about 50 weight percent. Generally the monovinylarene monomer is present in the final block copolymer in an amount in the range of from about 5 weight percent to about 95 weight percent based on the total weight of the final block copolymer, preferably in the range of from about 55 weight percent to about 95 weight percent, and more preferably in the range of from 60 weight percent to 95 weight percent.

Generally the conjugated diene monomer will be present in the final block copolymer in an amount in the range of from about 95 weight percent to about 5 weight percent based on the total weight of the final block copolymer, preferably in the range of from about 45 weight percent to about 5 weight percent, and more preferably in the range of from 40 weight percent to 5 weight percent.

The initiator can be any of the organomonoalkali metal compounds known for such purposes. Small amounts of polar organic compounds, such as ethers, thioethers, and tertiary amines can be employed in the hydrocarbon diluent to improve the effectiveness of the initiator and to randomize at least part of the monovinylarene monomer in a mixed monomer charge.

The polymerization process is carried out in a hydrocarbon diluent at any suitable temperature in the range of from about -100° C. to about 150° C., preferably in the range of from 0° C. to 125° C., at pressures sufficient to maintain the reaction mixture substantially in the liquid phase. After polymerization is complete, a coupling agent can be added.

After the polymerization and coupling, if employed, is complete, the stabilizing mixture can then be combined with the polymerization reaction solution by any means known in the art.

The organic phosphite and the hindered phenolic compound are employed in an amount effective to increase thermal stability. Generally the organic phosphite will be present in the copolymer resin in an amount in the range of about 0.05 to about 2 parts by weight per hundred parts by weight of resin (phr), more preferably in the range of about 0.1 phr to about 1 phr.

Generally the phenolic compound will be present in the copolymer resin in an amount in the range of from about 0.05 phr to about 0.5 phr, more preferably in the range of about 0.1 phr to about 0.25 phr.

The stabilized copolymer composition can be recovered and worked into the desired shape, such as by milling, extrusion, or injection molding. The copolymer composition can contain in addition to the stabilizer or stabilizers other additives such as fillers, extenders, dyes, vulcanizing agents, and accelerators, and the like.

The following examples are presented to further illustrate the invention and are not meant to limit the scope thereby.

Example I

This example demonstrates the low solubility of tetrakis [3-(3,5-di-t-butyl-4-hydroxyphenyl)propionyloxymethyl]methane, (commercially available as Irganox 1010 from Ciba Geigy) in cyclohexane.

Various solutions of Irganox 1010 in cyclohexane were prepared by adding excess Irganox to cyclohexane and warming the mixture until all of the Irganox 1010 was dissolved. The solutions were then cooled to a predetermined test temperature and allowed to equilibrate for at least 5 days, while the excess Irganox 1010 precipitated out of solution. The weight percent of Irganox 1010 in cyclohexane solution was determined gravimetrically using a DuPont 951 TGA. Samples of the clear supernatant, 80 mg each, were heated at 10° C. per minute and flushed with nitrogen at 100 mL per minute to drive off the cyclohexane. The weight of the residue at 200° C. was taken as the weight of Irganox 1010. The results are tabulated in the table below.

TABLE 1

| Sample No. | Solution Temp. (C.°) | Irganox 1010 Weight % |
|---|---|---|
| 101 | 23 | 1.2 |
| 102 | 35 | 3.6 |

TABLE 1-continued

| Sample No. | Solution Temp. (C.°) | Irganox 1010 Weight % |
|---|---|---|
| 103 | 40 | 4.3 |
| 104 | 54 | 22.8 |
| 105 | 62 | 46.9 |

It can be seen from Table 1 that Irganox 1010 is not appreciably soluble in cyclohexane at about 50° C. The combination of low solubility of the hindered phenolic compound and the high vapor pressure and low boiling point (80° C.) of cyclohexane make the use of an Irganox 1010 cyclohexane solution impossible without high pressure equipment. The precipitation of Irganox 1010 from the cyclohexane solution when employed in large scale processes, causes plugging of transfer lines.

Example II

Styrene/butadiene block copolymer was prepared employing a sequential solution polymerization and three initiator charges according to the process described in U.S. Pat. No.4,584,346. The polymerization was conducted under nitrogen in a 100 gallon (378 L) reactor with agitator and internal cooling coils employing essentially anhydrous conditions. Styrene (S), butadiene (B), initiator (i), and coupling agent (ca) were charged in the following sequence: S, i, i, S, B, I, S, B, ca. Polymerization was allowed to continue to completion after each monomer charge. Polymerization temperatures ranged from about 38° C. to about 110° C. and the pressure ranged from about 2 psig (14 kPa) to about 60 psig (413 KPa). The weight ratio of styrene to butadiene in the final styrene/butadiene block copolymer was 75/25. After the reactor temperature peaked and polymerization was essentially complete, 0.72 kg Vikoflex 7170 (0.4 phm), (a coupling agent comprising epoxidized soybean soil sold by Viking Chemical Co.) were charged to the reactor. Each charge was followed by a cyclohexane flush. After completion of the coupling reaction, the polymerization reaction was terminated by adding 0.2 phm water and $CO_2$.

A stabilizing mixture was prepared by heating 34.0 kg tris(nonylphenyl) phosphite (TNPP) (0.5 phm) to 105° C. with stirring. A slight positive nitrogen flow was introduced as pressure was flared off the vessel. Then 13.6 kg Irganox 1010 (0.20 phm) was added to the vessel and stirred for two hours to form a solution. The solution was cooled to about 60° C.

Then 0.63 kg of the above described stabilizing mixture was added to the polymerization reaction mixture. The block copolymers thus produced were recovered. The block copolymers exhibited melt flows in the range of from 6 g/10 min. to 8 g/10 min. measured according to ASTM D-1238, Condition 200/5.0.

Example III

A sequential polymerization was conducted as described for Example II with the exception that a 10 weight percent solution of Irganox 1010 in cyclohexane was employed. The Irganox 1010 precipitated from solution and plugged transfer lines, which required dismantling of the lines.

That which is claimed is:

1. A process for stabilizing polymers comprising:
   (1) contacting at least one hindered phenolic compound and an organic phosphite to form a stabilizing mixture, wherein said contacting is at a temperature sufficient to at least partially dissolve said hindered phenolic compound, wherein said organic phosphite is represented by the formula (RO)₃P, wherein each R is individually selected and is an alkyl, aryl, cycloalkyl, arylalkyl, or alkylaryl radical containing 1 to 20 carbon atoms, wherein said stabilizing mixture is essentially free of organic solvent other than the organic phosphite; and (2) contacting said stabilizing mixture and a polymeric composition comprising a monovinylarene/-conjugated diene copolymer;

wherein said organic phosphite and said at least one hindered phenolic compound are present in step (2) in an effective amount sufficient to stabilize said polymeric composition.

2. A process according to claim 1 wherein said contacting in step (1) is conducted at a temperature in the range of from the temperature at which said at least one hindered phenolic compound partially dissolves in said organic phosphite and up to about 50° C. above such temperature.

3. A process according to claim 2 wherein said contacting in step (1) is conducted at a temperature in the range of from the temperature at which said at least one hindered phenolic compound partially dissolves in said organic phosphite and up to about 40° C. above such temperature.

4. A process according to claim 3 wherein said contacting in step (1) is conducted at a temperature in the range of from the temperature at which said at least one hindered phenolic compound partially dissolves in said organic phosphite and up to 30° C. above such temperature.

5. A process according to claim 1 wherein said at least one hindered phenolic compound is tetrakis[3-(3,5-di-t-butyl-4-hydroxyphenyl)propionyloxymethyl]methane.

6. A process according to claim 5 wherein said contacting in step (1) is conducted at a temperature in the range of from about 90° C. to about 140° C.

7. A process according to claim 6 wherein said contacting in step (1) is conducted at a temperature in the range of from about 90° C. to about 130° C.

8. A process according to claim 7 wherein said contacting in step (1) is conducted at a temperature in the range of from 90° C. to 120° C.

9. A process according to claim 1 wherein said at least one hindered phenolic compound is n-octadecyl 3-(3,5-di-t-butyl-4-hydroxyphenyl)propionate.

10. A process according to claim 9 wherein said contacting in step (1) is conducted at a temperature in the range of from about 50° C. to about 100° C.

11. A process according to claim 10 wherein said contacting in step (1) is conducted at a temperature in the range of from about 50° C. to about 90° C.

12. A process according to claim 11 wherein said contacting in step (1) is conducted at a temperature in the range of from 50° C. to 80° C.

13. A process according to claim 1 wherein said at least one hindered phenolic compound is 2-(2-hydroxy-3-t-butyl-5-methylbenzyl)-4-methyl-6-t-butylphenyl acrylate.

14. A process according to claim 13 wherein said contacting in step (1) is conducted at a temperature in the range of from about 90° C. to about 140° C.

15. A process according to claim 14 wherein said contacting in step (1) is conducted at a temperature in the range of from about 90° C. to about 130° C.

16. A process according to claim 15 wherein said contacting in step (1) is conducted at a temperature in the range of from 90° C. to 120° C.

17. A process according to claim 1 wherein said at least one hindered phenolic compound is a mixture of n-octadecyl 3-(3,5-di-t-butyl-4-hydroxyphenyl)propionate and 2-(2-hydroxy-3-t-butyl-5-methylbenzyl)-4-methyl-6-t-butylphenyl acrylate.

18. A process according to claim 1 wherein the weight ratio of said at least one hindered phenolic compound to said organic phosphite is in the range of about 0.01:1 to about 1:1.

19. A process according to claim 18 wherein the weight ratio of said at least one hindered phenolic compound to said organic phosphite is in the range of about 0.05:1 to about 0.8:1.

20. A process according to claim 19 wherein the weight ratio of said at least one hindered phenolic compound to said organic phosphite is in the range of 0.1:1 to 0.7:1.

21. A process according to claim 1 wherein said organic phosphite is present in an amount in the range of about 0.05 to about 2 parts by weight per hundred parts by weight of resin.

22. A process according to claim 1 wherein said at least one hindered phenolic compound is present in an amount in the range of about 0.05 to about 0.5 parts by weight per hundred parts by weight of resin.

23. A process according to claim 1 wherein at least one of said R radicals in said organic phosphite contains an aryl group.

24. A process according to claim 23 wherein each said R radical in said organic phosphite contains from 1 to 15 carbon atoms.

25. A process according to claim 24 wherein said organic phosphite is tris(nonylphenyl) phosphite.

26. A process according to claim 1 wherein said stabilizing mixture is essentially free of organic solvent having a boiling point of less than about 100° C. other than the organic phosphite.

27. A process according to claim 1 wherein said hindered phenolic compound exhibits a solubility of less than about 50 weight percent in organic solvents having a boiling point of less than about 100° C.

28. A process according to claim 1 wherein said polymer composition contains monovinylarene monomer in an amount in the range of from about 5 weight percent to about 95 weight percent based on the total weight of the final copolymer and said conjugated diene is present in an amount in the range of from about 95 weight percent to about 5 weight percent based on the total weight of the final copolymer.

29. A process according to claim 28 wherein said polymer composition contains monovinylarene monomer in an amount in the range of from about 55 weight percent to about 95 weight percent based on the total weight of the final copolymer and said conjugated diene is present in an amount in the range of from about 45 weight percent to about 5 weight percent based on the total weight of the final copolymer.

30. A process according to claim 29 wherein said polymer composition contains monovinylarene monomer in an amount in the range of from 60 weight percent to 95 weight percent based on the total weight of the final copolymer and said conjugated diene is present in an amount in the range of from 40 weight percent to 5 weight percent based on the total weight of the final copolymer.

31. A process for stabilizing polymers comprising:
   (1) contacting at least one hindered phenolic compound and an organic phosphite to form a stabilizing mixture, wherein said contacting is at a temperature sufficient to at least partially dissolve said hindered phenolic compound,
   wherein said at least one hindered phenolic compound is tetrakis[3-(3,5-di-t-butyl-4-hydroxyphenyl)propionyloxymethyl]methane,
   wherein said organic phosphite is tris(nonylphenyl) phosphite,
   wherein said stabilizing mixture is essentially free of organic solvent other than the organic phosphite; and
   (2) contacting sad stabilizing mixture and a polymeric composition comprising a monovinylarene/conjugated diene copolymer;
   wherein said organic phosphite and said at least one hindered phenolic compound are present in step (2) in an effective amount sufficient to stabilize said polymeric composition.

32. A process for stabilizing polymers consisting essentially of:
   (1) contacting a stabilizing mixture consisting essentially of a hindered phenolic compound and an organic phosphite, wherein said contacting is at a temperature sufficient to at least partially dissolve said hindered phenolic compound,
   wherein said hindered phenolic compound is tetrakis[3-(3,5-di-t-butyl-4-hydroxyphenyl)propionyloxymethyl]methane,
   wherein said organic phosphite is tris(nonylphenyl) phosphite,
   (2) contacting said stabilizing mixture and a polymeric composition comprising a monovinylarene/-conjugated diene copolymer;
   wherein said organic phosphite and said hindered phenolic compound are present in step (2) in an effective amount sufficient to stabilize said polymeric composition.

33. A process for stabilizing polymers consisting essentially of:
   (1) contacting a stabilizing mixture consisting essentially of at least one hindered phenolic compound and an organic phosphite, wherein said contacting is at a temperature sufficient to at least partially dissolve said hindered phenolic compound,
   wherein said at least one hindered phenolic compound is a mixture of tetrakis [3-(3,5-di-t-butyl-4-hydroxyphenyl )propionyloxymethyl]methane and 2-(2hydroxy-3-t-butyl-5-methylbenzyl)-4-methyl-6-t-butylphenyl acrylate,
   wherein said organic phosphite is tris(nonylphenyl) phosphite,
   (2) contacting the product of (1) and a polymeric solution composition comprising a monovinylarene/conjugated diene copolymer;
   wherein said organic phosphite and said hindered phenolic compound are present in step (2) in an effective amount sufficient to stabilize said polymeric composition.

34. A process for preparing a stabilizing mixture capable of stabilizing polymers, said process consisting essentially of:
   (1) contacting at least one hindered phenolic compound and an organic phosphite at a temperature sufficient to at least partially dissolve said hindered phenolic compound to form said stabilizing mixture,
   wherein said organic phosphite is represented by the formula $(RO)_3P$, wherein each R is individually selected and is an alkyl, aryl, cycloalkyl, arylalkyl, or alkylaryl radical containing 1 to 20 carbon atoms,
   wherein said stabilizing mixture is essentially free of organic solvent.

* * * * *